United States Patent [19]

Andrean et al.

[11] Patent Number: 5,451,254

[45] Date of Patent: Sep. 19, 1995

[54] FINE DISPERSION OF MELANIN PIGMENTS, ITS PREPARATION AND ITS USE IN COSMETICS

[75] Inventors: Hervé Andrean, Paris; Didier Candau, Melun; Myrian Mellul, L'Hay-les-Roses; Christos Papantoniou, Montmorency; Bertrand Piot, La Carenne-Colombes, all of France

[73] Assignee: L'Oreal, Paris, France

[21] Appl. No.: 211,168

[22] PCT Filed: Sep. 16, 1992

[86] PCT No.: PCT/FR92/00868

§ 371 Date: Sep. 19, 1994

§ 102(e) Date: Sep. 19, 1994

[87] PCT Pub. No.: WO93/05754

PCT Pub. Date: Apr. 1, 1993

[30] Foreign Application Priority Data

Sep. 18, 1991 [FR] France .................. 91 11514

[51] Int. Cl.⁶ .............................................. A61K 7/13
[52] U.S. Cl. ..................................... 106/503; 106/311; 106/494; 106/498; 106/502; 106/504; 8/405; 8/406; 8/414; 8/416; 8/423; 424/70.7; 424/70.9
[58] Field of Search ............... 106/503, 494, 498, 502, 106/504, 311; 8/405, 406, 414, 416, 423; 424/70; 132/38

[56] References Cited

U.S. PATENT DOCUMENTS 5,205,837  4/1993  Andrean et al. ............... 8/405

FOREIGN PATENT DOCUMENTS

| | | |
|---|---|---|
| 0042816 | 12/1981 | European Pat. Off. . |
| 0313380 | 4/1989 | European Pat. Off. . |
| 0386680 | 9/1990 | European Pat. Off. . |
| 0441689 | 8/1991 | European Pat. Off. . |
| 0467767 | 1/1992 | European Pat. Off. . |
| 2207153 | 1/1989 | United Kingdom . |
| 9001919 | 3/1990 | WIPO . |
| 9205761 | 4/1992 | WIPO . |

*Primary Examiner*—Mark L. Bell
*Assistant Examiner*—Scott L. Hertzog
*Attorney, Agent, or Firm*—Cushman Darby & Cushman

[57] ABSTRACT

The invention relates to a dispersion of melanic pigments containing in a medium selected amongst: a) the straight or branched monoalcohols comprising at least 3 carbon atoms; the straight or branched polyols comprising at least 2 carbon atoms; the saturated or unsaturated cycloaliphatic alcohols comprising at least 6 carbon atoms; the aromatic alcohols comprising at least 6 carbon atoms; the $C_8$–$C_{22}$ fatty acid esters and $C_1$–$C_6$ alcohol esters or the $C_2$–$C_6$ polyol esters; the $C_1$–$C_6$ aliphatic acid esters or the $C_8$–$C_{22}$ aromatic acid and fatty alcohol esters; the $C_8$–$C_{22}$ fatty acid esters and the $C_8$–$C_{22}$ fatty alcohol esters, the $C_6$–$C_{22}$ polyacid and alcohol esters, the hydroxylated fatty acid diesters; the straight or branched paraffins comprising at least 8 carbon atoms; the silicone oils; and the mixture of these different organic compounds, or b) an emulsion comprised of a liquid defined under a), non water miscible, water and an emulsifying agent, a melanic pigment in the form of particles in which at least 75% of the particles have a grain size smaller than 10 microns. The invention also relates to a method for the preparation and the utilization of such dispersion in cosmetics.

22 Claims, No Drawings

FINE DISPERSION OF MELANIN PIGMENTS, ITS PREPARATION AND ITS USE IN COSMETICS

The subject of the present invention is a fine dispersion of melanin pigments, the process for its preparation and its use in cosmetics.

Melanin pigments are pigments which are known per se. More particularly, they are pigments which are at the origin of the coloration of hair, skin or hairs of human or animal origin. They may also be prepared by synthesis, in particular by oxidation of indole derivatives such as, more particularly, 5,6-dihydroxyindole.

Melanin pigments having a small particle size are particularly valuable insofar as they have a good covering power, which makes it possible for them to be used in lower concentrations compared with pigments having a larger particle size with a view to obtaining the same coloration.

The value of pigments having a small particle size also resides in their cosmetic characteristics, especially regarding the feel. The compositions based on pigments of small particle size have, in effect, a softer feel.

The known melanin pigments generally have a particle size between 100 and 150 microns and must be ground, for example in a mortar, by a grinder, by micronization or by other grinding techniques, in order to obtain particles having a particle size between 15 and 25 microns.

In order to obtain a smaller particle size, it is again necessary to grind these pigments, which is generally carried out in aqueous medium. However, a reagglomeration of the various particles is observed following this grinding and even after drying of the pigment.

The cosmetic compositions containing pigments presented in this manner often have poor cosmetic characteristics, insofar as the particles are relatively large and irregular. Due to the agglomeration, the compositions are visually appealing, often poorly stable and cover poorly.

The Applicant has observed that by carrying out the grinding of the melanin pigment in a specific medium, it was possible to obtain a fine dispersion of a melanin pigment, which is stable with time and does not reagglomerate. Moreover, the dispersion thus obtained has the advantage of being able to be used as it is in cosmetic compositions without it being necessary to isolate, dry and resuspend the pigment.

Moreover, these dispersions have improved antioxidant properties.

A subject of the invention is thus a stable dispersion of melanin pigments, having a very fine particle size, of low dispersity in a medium as defined below.

Another subject of the invention consists of the process for the preparation of such a dispersion.

A subject of the invention is also the use of this dispersion in the preparation of cosmetic compositions and the cosmetic compositions using this dispersion.

Other subjects of the invention will become apparent on reading the description and the examples which follow.

The process for the preparation of the dispersions of melanin pigments in accordance with the invention consists in grinding a melanin pigment in a liquid medium consisting of:
a) a liquid chosen from:
a linear or branched monoalcohol containing at least 3 carbon atoms;
a linear or branched polyol containing at least 2 carbon atoms;
a saturated or unsaturated cycloaliphatic alcohol containing at least 6 carbon atoms;
an aromatic alcohol containing at least 6 carbon atoms;
an ester of a $C_8$–$C_{22}$ fatty acid and a $C_1$–$C_6$ alcohol or a $C_2$–$C_6$ polyol, an ester of a $C_1$–$C_6$ aliphatic acid or an aromatic acid and a $C_8$–$C_{22}$ fatty alcohol, an ester of a $C_8$–$C_{22}$ fatty acid and a $C_8$–$C_{22}$ fatty alcohol, an ester of a polyacid and a $C_6$–$C_{22}$ alcohol, a diester of a hydroxylated fatty acid;
a linear or branched paraffin containing at least 8 carbon atoms;
a silicone oil;
or a mixture of one or more of the compounds defined above, or
b) an emulsion consisting of a water-immiscible liquid defined above, water and an emulsifying agent.

The melanin pigment is present in the liquid phase used during the grinding step at a concentration generally between 5 and 50% and preferably between 15 and 35%.

The process is implemented at a temperature between room temperature and 110° C. The grinding means preferably consist of a grinder containing beads. Zirconium oxide beads, glass beads or sand are more particularly used.

The duration of the grinding depends on the nature of the pigment, the size of the melanin pigment particles, the nature of the liquid medium and the grinding parameters. The duration is generally between 15 minutes and 24 hours and more preferably between 30 minutes and 9 hours.

A grinder containing beads sold under the name DYNOMILL, type KDL Special, for which the beads are made of zirconium oxide, having a diameter between 1 and 1.25 mm, is preferably used.

According to a preferred implementation of the process, preparation of the melanin pigment dispersions in accordance with the invention is carried out by dispersing, in a first step, melanin pigments preferably having a particle size between 15 and 20 microns in the grinding liquid medium as defined above in the presence of beads such as, more particularly, zirconium oxide beads and the grinding is then performed until at least 75% of the particles have a particle size lower than 10 microns and preferably at least 85% of the particles have a particle size lower than 5 microns.

According to a preferred mode, approximately 1 part of melanin pigment having a particle size of 15 to 25 microns is dispersed in approximately 2 parts of liquid medium defined above. The grinding is then performed in the presence of approximately 3 parts of beads.

The grinding medium defined is liquid. If solid compounds are used at room temperature, it will be necessary to heat the medium to a temperature which is slightly higher than the melting point of these compounds before dispersing the melanin pigment in this medium and carrying out the grinding.

The melanin pigment used in accordance with the invention may be of natural or synthetic origin. The synthetic pigments are in particular pigments resulting from the oxidative polymerization of an indole compound corresponding to the formula:

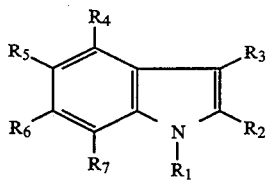 (I)

in which:

$R_1$ and $R_3$ represent, independently of each other, a hydrogen atom or a $C_1$–$C_4$ alkyl group;

$R_2$ represents a hydrogen atom, a $C_1$–$C_4$ alkyl group, a carboxyl group or a ($C_1$–$C_4$ alkoxy)carbonyl group;

$R_4$ and $R_7$ represent, independently of each other, a hydrogen atom, a hydroxyl group, a $C_1$–$C_4$ alkyl group, an amino group, a $C_1$–$C_4$ alkoxy group, a ($C_2$–$C_4$ acyl)oxy group or a ($C_2$–$C_4$ acyl)amino group;

$R_5$ represents a hydrogen atom, a hydroxyl group, a $C_1$–$C_4$ alkoxy group, a $C_1$–$C_4$ alkyl group, a halogen atom, an amino group, a ($C_2$–$C_{14}$ acyl)oxy group, a ($C_2$–$C_4$ acyl)amino group or a trimethylsilyloxy group;

$R_6$ represents a hydrogen atom, a hydroxyl group, a $C_1$–$C_4$ alkoxy group, an amino group, a ($C_2$–$C_4$ acyl)oxy group, a ($C_2$–$C_4$ acyl)amino group, a trimethylsilyloxy group or a ($C_2$–$C_4$ hydroxyalkyl)amino group;

it is also possible for $R_5$ and $R_6$ to form, together with the carbon atoms to which they are attached, a carbonyldioxy ring;

at least one of the radicals $R_4$ to $R_7$ represents a group OZ or $NHR_8$, no more than one of the radicals $R_4$ to $R_7$ representing $NHR_8$ and no more than two of the radicals $R_4$ to $R_7$ representing OZ and, in the case where Z represents a hydrogen atom, the two OH groups are in positions 5 and 6; and at least one of the radicals $R_4$ to $R_7$ represents a hydrogen atom, and in the case where only one of these radicals $R_4$ to $R_7$ represents a hydrogen atom, then only one radical among $R_4$ to $R_7$ represents $NHR_8$ or OZ, the other radicals representing a $C_1$–$C_4$ alkyl group;

the radical $R_8$ of the group $NHR_8$ denoting a hydrogen atom, a $C_2$–$C_4$ acyl or $C_2$–$C_4$ hydroxyalkyl group, and the radical Z of the group OZ denoting a hydrogen atom, a $C_2$–$C_{14}$ acyl group, a $C_1$–$C_4$ alkyl group or a trimethylsilyl group, and their salts with alkali metals, alkaline-earth metals, ammonium or amines.

The indole compounds of formula (I) above are chosen from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-ethoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-bis(trimethylsilyloxy)indole, the phosphoric ester of 5,6-dihydroxyindole, 5,6-dibenzyloxyindole, and the addition salts of these compounds.

The particularly preferred indole compounds are: 5,6-dihydroxyindole, 6-hydroxyindole, 7-hydroxyindole, 2-methyl-5,6-dihydroxyindolehydrobromide, 7-aminoindole, 3-methyl-5,6-dihydroxyindole, 4-hydroxy-5-methoxyindole and 2,3-dimethyl-5-methoxy-6-hydroxyindole.

The oxidative polymerization of the compounds of formula (I) may be carried out in aqueous medium, water/solvent(s), or solvent(s) open to the air, in the presence or absence of an alkaline agent and/or of an oxidizing agent such as hydrogen peroxide, preferably in the presence of an alkaline agent such as aqueous ammonia or in the presence of iodide ions, the iodide preferably being an alkali metal, alkaline-earth metal or ammonium iodide.

Oxidation of the compound of the formula (I) may also be carried out using periodic acid and its water-soluble salts and derivatives, permanganates and dichromates, such as those of sodium or potassium, sodium hypochlorite, ammonium persulphate, sodium nitrite and organic oxidizing agents chosen from ortho- and parabenzoquinones, ortho- and para-benzoquinone-mono- or -diimines, 1,2- and 1,4-naphthoquinones, 1,2- and 1,4-naphthoquinone-mono- or -diimines, such as those described in the Application EP-A-0,376,776. The preferred periodic acid salt is sodium periodate.

It is possible to activate the oxidizing agents with a pH modifier.

The preferred oxidative polymerization process uses hydrogen peroxide in the presence of aqueous ammonia. This oxidation is generally carried out at a temperature of the order of 20° C. to 100° C., and preferably 60° C. to 90° C.

The oxidative polymerization is preferably achieved by introducing the indole compound of formula (I) into an aqueous medium, or into a mixture of water and one or more solvents which may contain up to 95% of solvent, or alternatively into one or more anhydrous solvents, that is to say containing less than 1% of water.

Among the solvents which may be used, there may be mentioned $C_1$–$C_4$ lower alcohols such as ethyl alcohol, propyl or isopropyl alcohol or tert-butyl alcohol, alkylene glycols such as ethylene glycol or propylene glycol, alkylene glycol alkyl ethers such as the monomethyl, monoethyl or monobutyl ethers of ethylene glycol, monomethyl ethers of propylene glycol and of dipropylene glycol, and esters such as methyl lactate. The preferred solvent medium is an aqueous alcoholic medium containing from 1 to 10% of ethyl alcohol.

Depending on the processes, the oxidizing agent and the indole compound of formula (I) are left in contact for a few minutes to a few days.

The basifying agents are preferably chosen from sodium hydroxide, alkali metal carbonates or aqueous ammonia, in proportions between $5 \times 10^{-4}\%$ to 10% by weight relative to the weight of the composition subjected to the oxidation.

When an iodide is used in the presence of hydrogen peroxide, sodium iodide or potassium iodide is preferably used at a concentration between 1 and 6%.

The colored pigment resulting from the oxidative polymerization is obtained in insoluble form. It is isolated by filtration or centrifugation. In order to remove traces of the unreacted compound of formula (I), the pigment may be rinsed with water before or after filtration or centrifugation.

In the case where a process of oxidative polymerization open to the air is used, it is also possible to isolate the pigment by freeze-drying.

A pigment is thus obtained having a particle size of 100–150 μm, which is then ground by a standard route as indicated above until its particle size is of the order of 15 to 25 μm.

According to the invention, the compounds used in the grinding medium by way of liquid medium also constitute the medium in which the finely ground melanin pigment is dispersed. When they are liquids, they are chosen from the abovementioned compounds, and preferably:

for linear or branched monoalcohols, from dodecanol or oleyl alcohol;

for linear or branched polyols, from propylene glycol or glycerine;

for cycloaliphatic alcohols, cyclohexanol will be chosen;

for aromatic alcohols, from benzyl alcohol and phenylethyl alcohol;

for esters, from isopropyl myristate and palmitate, $C_8$–$C_{12}$ fatty acid triglycerides such as the product called MIGLYOL, triolein, octyl stearate, fatty alcohol benzoates such as the product called FINSOLV, sold by the company FINETEX, pentaerythritol tetracaprylate/caprate or pentaerythritol tetraisostearate;

for silicones, from polyorganosiloxanes in oil form. More particularly these are polyalkylsiloxanes, polyarylsiloxanes, polyalkylarylsiloxanes, silicone gums and resins mixed with volatile silicones, polyorganosiloxanes modified by oxyethylenated and/or oxypropylenated groups, and cyclomethicones.

When the medium consists of an emulsion, the liquids are preferably chosen from those mentioned above with the exclusion of linear or branched polyols, one or more emulsifying agents and water. The emulsifying agents are well known in the state of the art. By way of reference, there may be mentioned those cited in the work Harry's Cosmeticology—7th edition, edited by J. B. Wilkinson and R. J. Moore—pages 626 to 638.

According to a preferred embodiment, when the grinding medium is an emulsion, the aqueous phase content of the latter does not exceed 50% by weight relative to the total weight of the emulsion, and in particular does not exceed 30%.

The melanin pigment is generally present in the final dispersion obtained in concentrations between 5 and 50% by weight, and preferably between 15 and 35% by weight relative to the total weight of the composition.

The composition which constitutes a subject of the invention takes the form of a dispersion, containing at least 75% of particles having a particle size lower than 10 μm, and preferably at least 85% of these particles have a particle size lower than 5 μm, in the medium defined above.

This dispersion is particularly stable with time, in particular its particle size remains constant. The phenomenon of reagglomeration is not observed.

The composition moreover has the advantage of being able to be used directly and as it is in cosmetic compositions.

This dispersion may constitute the black pigment which is preponderant in cosmetic compositions.

It may more particularly be used in make-up compositions (mascaras, eye-liners, eyeshadows or rouges, foundations, lipsticks, nail varnishes and powders), in sun care compositions or in compositions for coloring the hair.

These compositions may take the form of more or less thick lotions, emulsions (milk or cream), a stick or a powder. The concentration of melanin pigments in these compositions, for which at least 75% of the particles have a particle size lower than 10 microns and preferably 85% have a particle size lower than 5 microns, is between 0.001 and 20% by weight.

Dilution of the dispersion of melanin pigment defined above, even in an aqueous medium, does not modify its quality in the sense that its particle size remains substantially constant without there being any reagglomeration and/or sedimentation.

When the compositions are used for making up the skin, the eyelashes and the eyebrows, they may take a solid or pasty, anhydrous or aqueous form and in particular may take the form of lipophilic, hydrophilic or hydrophilic/lipophilic dispersions, containing the particles may defined above in one or other of the phases or in them both.

The compositions have the advantage of being particularly stable and of having a good level of harmlessness.

When the compositions are used for the protection of human skin against UV rays, they constitute so-called "sun care" compositions and they are generally present in the form of dispersions in solvents or in fatty substances, or alternatively in the form of emulsions such as creams and milks, ointments, gels, small solid sticks or aerosol foams.

When they are used in the form of emulsions, they may in addition contain surface-active agents which are well known in the state of the art, such as anionic, nonionic, cationic or amphoteric surface-active agents.

The make-up compositions and the sun care compositions may also contain fatty substances, organic solvents, silicones, thickeners, emollients, sun filters, antifoaming agents, moisturizing agents, perfumes, preservatives, antioxidizing agents, fillers, sequestering agents, treating agents such as anionic, cationic, nonionic or amphoteric polymers or their mixtures, propellants and basifying or acidifying agents, in addition to the medium used for the grinding and which constitutes the dispersion medium.

The fatty substances may consist of an oil or a wax or their mixture, fatty acids, fatty alcohols, petrolatum, paraffin, lanolin, hydrogenated lanolin or acetylated lanolin.

The oils are in particular chosen from animal, vegetable, mineral or synthetic oils and especially hydrogenated palm oil, hydrogenated castor oil, liquid paraffin, paraffin oil and Purcellin oil.

The waxes are especially chosen from animal, lignite, vegetable, mineral or synthetic waxes, and beeswaxes, carnauba, candelilla, sugar cane or Japan waxes, ozocerites, montan wax, microcrystalline waxes, paraffins and silicone waxes may be mentioned.

The compositions in accordance with the invention may also contain, in addition to the melanin pigments, other pigments generally used in cosmetics, especially pearlescent pigments and/or nacreous agents which make it possible to vary the colorations which are likely to be obtained or of increasing the protection with regard to ultraviolet rays. In this latter case, metallic pigments such as the oxides of titanium, zinc, cerium or zirconium are used.

"Nanopigments" are preferably used, of particle size lower than 100 nm and preferably between 5 and 50 nm. The nanopigments may be coated or non-coated.

A subject of the invention is also a process for making up the skin, for protecting human skin against the harmful effects of UV rays or for coloring hair, using the compositions containing, at least in part, the dispersion of melanin pigments as defined above.

The examples which follow are intended to illustrate the invention without in any way presenting a limiting nature.

EXAMPLES OF PREPARATION OF THE DISPERSION

PREPARATION EXAMPLE 1

A) PREPARATION OF THE SYNTHETIC MELANIN PIGMENT 500 g of 5,6-dihydroxyindole are dissolved in 5 liters of water. 5 ml of aqueous ammonia solution at a concentration of 20% are added and the whole is brought to 80° C. The mixture consisting of 390 ml of water and 470 g of hydrogen peroxide solution at a concentration of 50% is added over two hours at this temperature. The heating is maintained for an additional two hours after the end of the addition.

The black precipitate is filtered off and then washed with water. The product is dried under vacuum. 498 g of pigment are isolated.

B) PRE-GRINDING

The pigment A) prepared above takes the form of coarse particles of diameter ranging up to 600 microns.

In a first stage, this pigment is ground as it is in a toothed roll crusher of the ALPINE 63 C type.

The pigment leaving the grinder has a particle size distribution curve centred at approximately 20 microns, according to measurements made on a MALVERN Mastersizer SB-OB apparatus.

The pigment is then ready for grinding.

C) PREPARATION OF THE DISPERSION

The pigment pre-ground according to step B), is ground in a grinder of DYNOMILL-KDL-Special type, which contains beads made of zirconium oxide of diameter 1 to 1.25 mm.

| Pigment | 300 g |
|---|---|
| Liquid phase | 700 g |
| Zirconium oxide beads | 1 kg |

The grinding is carried out at room temperature for 7 hours, in the various media indicated below.

| PREPARATION EXAMPLES | 1 | 2 |
|---|---|---|
| PIGMENT OBTAINED IN STEP B | 30 | 30 |
| PROPYLENE GLYCOL | 70 | |
| TRIGLYCERIDE OF CAPRIC/CAPRYLIC ACID SOLD BY HULS UNDER THE NAME MIGLYOL 812 | | 70 |

These compositions are particularly stable on storage.

PREPARATION EXAMPLE 3

The procedure is performed as for Examples 1 and 2 above, using liquid paraffin as dispersion liquid. A fine and stable black dispersion is obtained.

PREPARATION EXAMPLE 4

30% of pigment obtained in step B) of Preparation Example 1 is mixed with 70% of silicone (decamethylpentacyclosiloxane).

70% of the above preparation are mixed with 30% of zirconium oxide beads.

The grinding is carried out at room temperature for 5 hours.

A fine and regular black dispersion is obtained.

PREPARATION EXAMPLE 5

The procedure is performed as for Example 4, replacing the silicone oil by the mixture: FINSOLV TN*/HEXYLENE GLYCOL 30/70.

The dispersion obtained is fine and stable, and black in color.

*FINSOLV TN=$C_{12}$–$C_{15}$ fatty alcohol benzoates.

PREPARATION EXAMPLE 6

The procedure is performed as in Examples 1 to 3, using as the dispersion mixture the emulsion obtained by mixing:

| Miglyol 812 | 90 g |
|---|---|
| Water | 21 g |
| Sorbitol monostearate (SPAN 60 sold by ICI) | 4.2 g |
| Oxyethylenated cetylstearyl alcohol containing 15 moles of ethylene/oxide | 4.2 g |

A fine and stable black dispersion is obtained.

APPLICATION EXAMPLE 1

PREPARATION OF A MASCARA

The composition of the mascara is:

| Triethanolamine stearate | 7 g |
|---|---|
| Beeswax | 4 g |
| Carnauba wax | 1 g |
| Paraffin | 6.5 g |
| Colophony | 0.7 g |
| Dispersion of melanin pigment in a liquid phase obtained according to step C) of Preparation Example 1 | |
| Hydrolysate of keratin, sold by CRODA under the name KERASOL | 2.0 g |
| Gum arabic | 0.5 g |
| Preservative qs | |
| Purified water qs | 100 g |

The triethanolamine stearate, waxes, paraffin and colophony are heated at 85° C. and then the dispersion of the melanin pigment is introduced thereto.

The aqueous phase containing the remainder of the formula is heated separately at 85° C. and then the two phases are mixed.

For these preparations, pigment dispersions prepared according to Examples 1 to 3 above are used.

Example 1a) contains the melanin dispersion in propylene glycol of Preparation Example 1.

Example 1b) contains the dispersion of melanin pigment in Miglyol 812 of Preparation Example 2.

The mascaras of Examples 1a) and 1b) are black in color. Examination under a microscope reveals a fine and regular dispersion. Application of the make-up to eyelashes is easy. The eyelashes are thickened and well separated. The make-up has a good staying power.

APPLICATION EXAMPLE 2

PREPARATION OF A MASCARA

The following composition is prepared:

| | |
|---|---|
| Carnauba wax | 5 g |
| Candelilla wax | 5 g |
| Ethyl alcohol | 3 g |
| Montmorillonite | 6 g |
| Dispersion containing 25% of a melanin pigment dispersed in liquid paraffin according to Preparation Example 3 | 3.5 g |
| Talc | 10 g |
| Isoparaffin qs | 100 g |

The procedure is as follows:

The waxes are heated at 80° C. The talc and the dispersion of melanin pigments are added. The montmorillonite and a part of the isoparaffin are subsequently incorporated. At approximately 40° C., the ethyl alcohol and the remainder of the isoparaffin are introduced. The whole mixture is passed to the grinder. In this case, a so-called "waterproof" (water-resistant) mascara is obtained.

APPLICATION EXAMPLE 3

In Application Example 2, the dispersion prepared according to Example 3 may be replaced by the dispersion prepared according to Example 6.

APPLICATION EXAMPLE 4

FOUNDATION

The following composition is prepared:

| | |
|---|---|
| Propylene glycol | 2 g |
| Magnesium aluminium [sic] | 1 g |
| Carboxymethyl cellulose | 0.2 g |
| Triethanolamine | 1 g |
| Stearic acid | 2.2 g |
| Glyceryl stearate | 2.2 g |
| Cyclomethicone | 10 g |
| 2-Ethylhexyl para-dimethylaminobenzoate | 0.5 g |
| 2-Hydroxy-4-methoxybenzophenone | 0.5 g |
| Product of Preparation Example 3 | 1.5 g |
| Glycerine | 3 g |
| Sodium lauryl sarcosinate | 0.6 g |
| Pigments | 10 g |
| Triglyceride of caprylic/capric acids | 15 g |
| Preservatives | 0.5 g |
| Water qs | 100 g |

The composition takes the form of a fine and regular dispersion which is stable after storage for 2 months.

APPLICATION EXAMPLE 5

MAKE-UP GEL FOR HAIR

The following composition is prepared:

| | |
|---|---|
| Crosslinked methacrylic acid/ethyl acrylate copolymer in anionic dispersion containing 38% of AS, sold under the name VISCOATEX 538 by the company COATEX | 3.95 g AS |
| Hydroxyethyl cellulose/diallyldimethylammonium chloride copolymer, sold under the name CELQUAT LOR by the company NATIONAL STARCH | 1.5 g |
| Ethanol | 10 g |
| Acrylate/t-octylpropenamide copolymer, Sold under the name DERMACRYL 79 by the company NATIONAL STARCH | 1.5 g |
| Stearyldimethylamine | 3.75 g |
| Melanin pigment ground in propylene glycol containing 20% of AS | 2.5 g AS |
| 2-Amino-2-methyl-1-propanol pH = 7.5 Preservative, sequestering agent, perfume qs | |
| Water qs | 100 g |

APPLICATION EXAMPLE 6

SUN CARE COMPOSITION

| | |
|---|---|
| Mixture of cetylstearyl alcohol and cetylstearyl alcohol 33 OE, sold under the name SYNNOWAX AO by the company HENKEL | 7 g |
| Non-autoemulsifiable mixture of glyceryl monostearate and distearate | 2 g |
| Cetyl alcohol | 1.5 g |
| Silicone oil | 1.5 g |
| Liquid paraffin | 7 g |
| Dispersion of melanin pigment obtained according to Example 3, diluted in liquid paraffin (1.25% by weight of melanin pigment) | 8 g |
| 2-Ethylhexyl para-methoxycinnamate, sold under the name PARSOL MCX by the company GIVAUDAN | 5 g |
| Glycerine | 20 g |
| Perfume, preservatives qs | |
| Water qs | 100 g |

We claim:

1. Dispersion of melanin pigments, characterized in that it contains, in a medium chosen from:
   a) liquids chosen from:
      linear or branched monoalcohols containing at least 3 carbon atoms;
      linear or branched polyols containing at least 2 carbon atoms;
      saturated or unsaturated cycloaliphatic alcohols containing at least 6 carbon atoms;
      aromatic alcohols containing at least 6 carbon atoms;
      esters of $C_8$–$C_{22}$ fatty acids and $C_1$–$C_6$ alcohols or $C_2$–$C_6$ polyols; esters of $C_1$–$C_6$ aliphatic acids or aromatic acids and $C_8$–$C_{22}$ fatty alcohols; esters of $C_8$–$C_{22}$ fatty acids and $C_8$–$C_{22}$ fatty alcohols, esters of $C_6$–$C_{22}$ alcohols and polyacids, and diesters of hydroxylated fatty acids;
      linear or branched paraffins containing at least 8 carbon atoms;
      silicone oils;
      and the mixture of these various compounds, or
   b) an emulsion consisting of a water-immiscible liquid defined above, water and an emulsifying agent,
   a melanin pigment in the form of particles, for which at least 75% of the particles have a particle size lower than 10 microns.

2. Dispersion according to claim 1, characterized in that at least 85% of the particles have a particle size lower than 5 microns.

3. Dispersion according to claim 1 characterized in that the concentration of melanin pigments in the dispersion is between 5 and 50% by weight relative to the total weight of the composition.

4. Process for the preparation of a dispersion according to claim 1 characterized in that, into a liquid medium chosen from:
a) a liquid chosen from:
a linear or branched monoalcohol containing at least 3 carbon atoms;
a linear or branched polyol containing at least 2 carbon atoms;
a saturated or unsaturated cycloaliphatic alcohol containing at least 6 carbon atoms;
an aromatic alcohol containing at least 6 carbon atoms;
an ester of a $C_8$-$C_{22}$ fatty acid and a $C_1$-$C_6$ alcohol or a $C_2$-$C_6$ polyol, an ester of a $C_1$-$C_6$ aliphatic acid or an aromatic acid and a $C_8$-$C_{22}$ fatty alcohol, an ester of a $C_8$-$C_{22}$ fatty acid and a $C_8$-$C_{22}$ fatty alcohol, an ester of a polyacid and a $C_6$-$C_{22}$ alcohol, a diester of a hydroxylated fatty acid;
a linear or branched paraffin containing at least 8 carbon atoms;
a silicone oil;
and the mixture of these various compounds, or
b) an emulsion consisting of a water-immiscible liquid defined above, water and an emulsifying agent,
there is introduced a melanin pigment of natural or synthetic origin and in that grinding is performed in a liquid medium until at least 75% of the particles have a particle size lower than 10 microns.

5. Process according to claim 4, characterized in that the melanin pigment introduced into the grinding medium has a particle size between 15 and 25 microns.

6. Process according to claim 4, characterized in that a melanin pigment of natural or synthetic origin is used.

7. Process according to claim 6, characterized in that the melanin pigment used is a pigment prepared by oxidative polymerization of an indole compound corresponding to the formula (I):

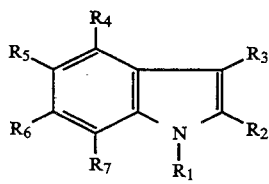

in which:
$R_1$ and $R_3$ represent, independently of each other, a hydrogen atom or a $C_1$-$C_4$ alkyl group;
$R_2$ represents a hydrogen atom, a $C_1$-$C_4$ alkyl group, a carboxyl group or a ($C_1$-$C_4$ alkoxy)carbonyl group;
$R_4$ and $R_7$ represent, independently of each other, a hydrogen atom, a hydroxyl group, a $C_1$-$C_4$ alkyl group, an amino group, a $C_1$-$C_4$ alkoxy group, a ($C_2$-$C_4$ acyl)oxy group or a ($C_2$-$C_4$ acyl)amino group;
$R_5$ represents a hydrogen atom, a hydroxyl group, a $C_1$-$C_4$ alkoxy group, a $C_1$-$C_4$ alkyl group, a halogen atom, an amino group, a ($C_2$-$C_{14}$ acyl)oxy group, a ($C_2$-$C_4$ acyl)amino group or a trimethylsilyloxy group;
$R_6$ represents a hydrogen atom, a hydroxyl group, a $C_1$-$C_4$ alkoxy group, an amino group, a ($C_2$-$C_4$ acyl)oxy group, a ($C_2$-$C_4$ acyl)amino group, a trimethylsilyloxy group or a ($C_2$-$C_4$ hydroxyalkyl)amino group;
it is also possible for $R_5$ and $R_6$ to form, together with the carbon atoms to which they are attached, a carbonyldioxy ring;
at least one of the radicals $R_4$ to $R_7$ represents a group OZ or $NHR_8$, no more than one of the radicals $R_4$ to $R_7$ representing $NHR_8$ and no more than two of the radicals $R_4$ to $R_7$ representing OZ and, in the case where Z represents a hydrogen atom, the two OH groups are in positions 5 and 6; and at least one of the radicals $R_4$ to $R_7$ represents a hydrogen atom, and in the case where only one of these radicals $R_4$ to $R_7$ represents a hydrogen atom, then only one radical among $R_4$ to $R_7$ represents $NHR_8$ or OZ, the other radicals representing a $C_1$-$C_4$ alkyl group;
the radical $R_8$ of the group $NHR_8$ denoting a hydrogen atom, a $C_2$-$C_4$ acyl or $C_2$-$C_4$ hydroxyalkyl group, and the radical Z of the group OZ denoting a hydrogen atom, a $C_2$-$C_4$ acyl group, a $C_1$-$C_4$ alkyl group or a trimethylsilyl group,
and their salts with alkali metals, alkaline-earth metals, ammonium or amines.

8. Process according to claim 7, characterized in that the indole compounds of formula (I) are chosen from: 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-ethoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-aminoindole-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-bis(trimethylsilyloxy)indole, the phosphoric ester of 5,6-dihydroxyindole, 5,6-dibenzyloxyindole, and the addition salts of these compounds.

9. Process according to claim 4, characterized in that the dispersion containing the melanin pigment to be ground is introduced into a grinder containing beads.

10. Process according to claim 4, characterized in that a grinder containing beads using zirconium oxide beads, glass beads or sand is used.

11. Process according to claim 4, characterized in that the composition subjected to the grinding contains 5 to 50% by weight of melanin pigments relative to the total weight of the composition.

12. Process according to claim 4, characterized in that the grinding temperature is between room temperature and 110° C. depending on whether the medium used for the grinding is solid or otherwise at room temperature.

13. Process according to claim 4, characterized in that the linear or branched monoalcohols are chosen from dodecanol and oleyl alcohol; the linear or branched polyols are chosen from propylene glycol or glycerine; the cycloaliphatic alcohol is cyclohexanol; the aromatic alcohols are chosen from benzyl alcohol or phenylethyl alcohol; the esters are chosen from isopropyl myristate and palmitate, $C_8$–$C_{12}$ fatty acid triglycerides, triolein, octyl stearate, fatty alcohol benzoates, pentaerythritol caprylate/caprate or pentaerythritol tetraisostearate; the silicones are polyorganosiloxanes in oil form.

14. Process according to claim 13, characterized in that the silicones are polyalkylsiloxanes, polyarylsiloxanes, polyalkylarylsiloxanes, silicone gums and resins mixed with volatile silicones, polyorganosiloxanes modified by oxyethylenated and/or oxypropylenated groups.

15. Dispersion obtained by the implementation of the process as defined in claim 4.

16. A make-up, sun care or hair coloring composition comprising the dispersion of claim 1.

17. Cosmetic composition, characterized in that it comprises, at least in part, a dispersion as defined in claim 1 in a cosmetically acceptable medium.

18. Composition according to claim 17, characterized in that it comprises melanin pigments in the form of particles, for which at least 75% of the particles have a particle size lower than 10 microns, in proportions between 0.001 and 20% by weight relative to the total weight of the composition.

19. Composition according to claim 17, intended to be used for making up skin, eyelashes and eyebrows, characterized in that it is present in solid or pasty, anhydrous or aqueous form.

20. Composition according to claim 17, intended for protecting human skin against UV rays, characterized in that it takes the form of a suspension in solvents or fatty substances, or takes the form of emulsions, ointments, gels, small solid sticks or aerosol foams.

21. Composition according to claim 17, characterized in that it contains contain fatty substances, organic solvents, silicones, thickeners, emollients, sun filters, antifoaming agents, moisturizing agents, perfumes, preservatives, antioxidizing agents, fillers, sequestering agents, treating agents, propellants and basifying or acidifying agents, or other pigments.

22. Composition according to claim 20, characterized in that it contains a nanopigment of metallic oxide chosen from the oxides of titanium, zinc, cerium or zirconium, these nanopigments having a mean diameter lower than 100 nm and being coated or non-coated.

* * * * *